United States Patent
Schmieding et al.

(10) Patent No.: US 8,702,752 B2
(45) Date of Patent: Apr. 22, 2014

(54) KNOTLESS ANCHOR FOR SURGICAL REPAIR

(75) Inventors: Reinhold Schmieding, Naples, FL (US); R. Donald Grafton, Naples, FL (US); Peter J. Dreyfuss, Naples, FL (US); Stephen S. Burkhart, San Antonio, TX (US)

(73) Assignee: Arthrex, Inc., Naples, FL (US)

( * ) Notice: Subject to any disclaimer, the term of this patent is extended or adjusted under 35 U.S.C. 154(b) by 1814 days.

(21) Appl. No.: 11/155,742

(22) Filed: Jun. 20, 2005

(65) Prior Publication Data

US 2005/0283156 A1      Dec. 22, 2005

Related U.S. Application Data

(60) Provisional application No. 60/580,349, filed on Jun. 18, 2004.

(51) Int. Cl.
*A61F 2/08*      (2006.01)
*A61B 17/04*      (2006.01)

(52) U.S. Cl.
USPC .......................... 606/232; 606/228

(58) Field of Classification Search
USPC ............ 606/232, 228, 151, 74, 144, 148, 213, 606/300
See application file for complete search history.

(56) References Cited

U.S. PATENT DOCUMENTS

| | | | |
|---|---|---|---|
| 5,259,846 A * | 11/1993 | Granger et al. ................ | 606/224 |
| 5,500,000 A * | 3/1996 | Feagin et al. ................. | 606/232 |
| 5,591,207 A | 1/1997 | Coleman | |
| 5,702,397 A * | 12/1997 | Goble et al. ................... | 606/232 |
| 5,810,854 A * | 9/1998 | Beach ............................ | 606/151 |
| 6,045,574 A * | 4/2000 | Thal .............................. | 606/232 |
| 6,139,565 A | 10/2000 | Stone et al. | |
| 6,156,039 A * | 12/2000 | Thal .............................. | 606/232 |
| 6,267,766 B1 * | 7/2001 | Burkhart ....................... | 606/232 |
| 6,527,794 B1 * | 3/2003 | McDevitt et al. ............. | 606/232 |
| 6,544,281 B2 * | 4/2003 | ElAttrache et al. ........... | 606/232 |
| 6,641,597 B2 * | 11/2003 | Burkhart et al. .............. | 606/232 |
| 6,761,722 B2 * | 7/2004 | Cole et al. ...................... | 606/74 |
| 6,887,259 B2 * | 5/2005 | Lizardi ......................... | 606/232 |
| 7,144,415 B2 * | 12/2006 | Del Rio et al. ................ | 606/232 |
| 7,981,140 B2 * | 7/2011 | Burkhart ....................... | 606/232 |
| 2002/0013608 A1 | 1/2002 | ElAttrache et al. | |
| 2003/0004545 A1 * | 1/2003 | Burkhart et al. .............. | 606/232 |
| 2003/0171778 A1 * | 9/2003 | Lizardi ......................... | 606/232 |
| 2005/0119696 A1 * | 6/2005 | Walters et al. ................ | 606/228 |

FOREIGN PATENT DOCUMENTS

| | | |
|---|---|---|
| EP | 1 199 035 | 4/2002 |
| EP | 1 206 924 | 5/2002 |
| WO | WO 2005/051205 | 6/2005 |

* cited by examiner

*Primary Examiner* — Mark Mashack
(74) *Attorney, Agent, or Firm* — Dickstein Shapiro LLP

(57) ABSTRACT

Knotless fixation of soft tissue to bone is accomplished using a bone anchor configured to provide interference fixation of a soft-tissue connector. The soft-tissue connector is provided in the form of a flat narrow piece of material. Additional fixation strength can be provided by configuring the bone anchor to penetrate into or through the soft-tissue connector. The bone anchor is installed into a pre-formed hole or socket in the bone.

3 Claims, 6 Drawing Sheets

KNOTLESS ANCHOR FOR SURGICAL REPAIR

This application claims the benefit of U.S. Provisional Appl. No. 60/580,349 filed Jun. 18, 2004, the disclosure of which is incorporated herein by reference.

BACKGROUND OF THE INVENTION

1. Field of the Invention

The present invention relates to apparatus and methods for tissue repair, and more particularly to techniques using knotless anchors for fixation of soft tissue to bone.

2. Description of the Related Art

When tissue structures such as tendons or ligaments ("soft" tissues), detach from bone-tissue structures ("hard" tissue), it may become necessary to reconnect the structures surgically. Techniques and devices that have been developed generally involve knotting suture to anchor the soft tissue to the hard tissue. Reattachment with suture, and the knot-tying involved, can present significant difficulties. Operating in the shoulder joint space, for example, particularly arthroscopic surgery, can be very challenging. It would be beneficial to surgically-anchor tissue torn from bone without the need to tie knots in suture.

Knotless methods and apparatus for attachment of soft and hard tissue structures are disclosed in U.S. Pat. No. 6,544,281 to ElAttrache et al, the entire disclosure of which is incorporated herein by reference. ElAttrache et al. discloses securing soft tissue to bone using lengths of suture thread. The suture thread is secured in a pre-formed socket with an anchor without the need for tying knots. The suture threads are held in place on the end of an inserter/driver using a loop of suture or by inserting ends of the suture into a distal cannula of the inserter/driver. Management of suture threads in certain surgical situations can be difficult and cumbersome. The need exists for simplified knotless anchoring apparatus and techniques that also provide broader surgical application and improved fixation strength.

BRIEF SUMMARY OF THE INVENTION

The present invention includes soft-tissue connectors, anchoring devices (anchors), instrumentation, and related surgical techniques and constructs used to secure suture to bone without the need to tie a knot in suture. An exemplary soft-tissue connector is provided in the form of a flat, narrow tape material. The tape material can be formed of suture can be configured as a webbing which is manufactured by weaving or braiding. Additionally, the soft-tissue connector can be a synthetic material for which weaving or braiding is not required. Further alternative types of soft-tissue connectors can include, without limitation, a portion or extension of the ligament, graft, or soft tissue to be fixed to bone.

The soft-tissue connector is attached to soft tissue and secured to bone using an anchoring device. The anchoring device is used to hold the soft-tissue connector in a pre-formed socket by interference fixation.

In one exemplary form, the anchoring device has a cannulated body. The cannula, formed axially through the anchor body, serves several purposes. The cannula receives an anchor driver and/or a soft-tissue connector holding device during installation. Additional anchoring fixation can be provided by a pin driven into tissue through the cannula. The anchor driver also can be cannulated to fit over a guide wire during installation.

The invention can be used for various reattachment purposes, including biceps tendon and rotator cuff. In an exemplary application, rotator cuff repair proceeds in the shoulder by attaching a length of soft-tissue connector to the rotator cuff. At least one limb of the soft-tissue connector extends from the attachment point on the rotator cuff. At least one pre-formed hole or socket is provided at the articular margin of the shoulder. A driver is fitted with the anchor and a guide wire. The point of the guide wire protrudes a few millimeters from the tip of the driver.

The limb of soft-tissue connector is extended across the pre-formed hole, and a length of the soft-tissue connector is urged into the pre-drilled socket to form a U-shaped open loop with the soft-tissue connector limb. The soft-tissue connector, preferably provided in the form of a flat, woven tape, extends generally down one side of the socket, across the bottom, and back up the other side. The length of soft-tissue connector required is adjusted so that the attached tissue is approximated toward the pre-drilled hole, adjacent the opening-edge. Instruments are provided for holding the appropriate length of soft-tissue connector in the socket prior to fixation with an anchor. With the soft-tissue connector limb held in place, the anchor is driven into the pre-drilled socket until the drive-end is flush with the outer surface of the surrounding bone.

Once the anchor is installed, the anchor driver is removed. The guide wire can be left in place. A cannulated pin is loaded onto the guide wire and driven into and through the cannulation of the anchor until the cannulated pin is flush with the surface of the surrounding bone. The cannulated pin pierces the soft-tissue connector to enhance fixation. The construct preferably rigidly secures a fixed length of soft-tissue connector to bone. Exposed extraneous soft-tissue connector is cut off flush to the bone surface.

DETAILED DESCRIPTION OF THE INVENTION

Figure 1:
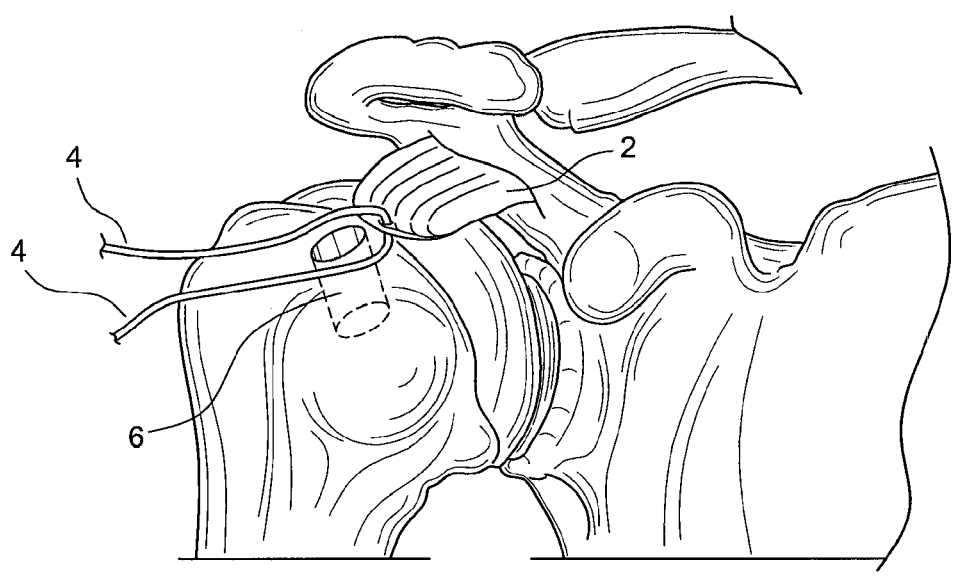
FIG. 1 is a perspective view depicting an initial step in a method of rotator cuff repair according to the present invention.

Referring initially to FIG. 1, repair of a torn rotator cuff 2 proceeds by passing a length of soft-tissue connector 4 through the detached portion of the rotator cuff 2. An exemplary soft-tissue connector 4 is marketed as Fibertape™ by Arthrex, Inc., Naples, Fla. A pre-formed socket 6 is created at the articular margin of the shoulder. The socket can be formed by drilling or core removal, for example.

Figure 2:
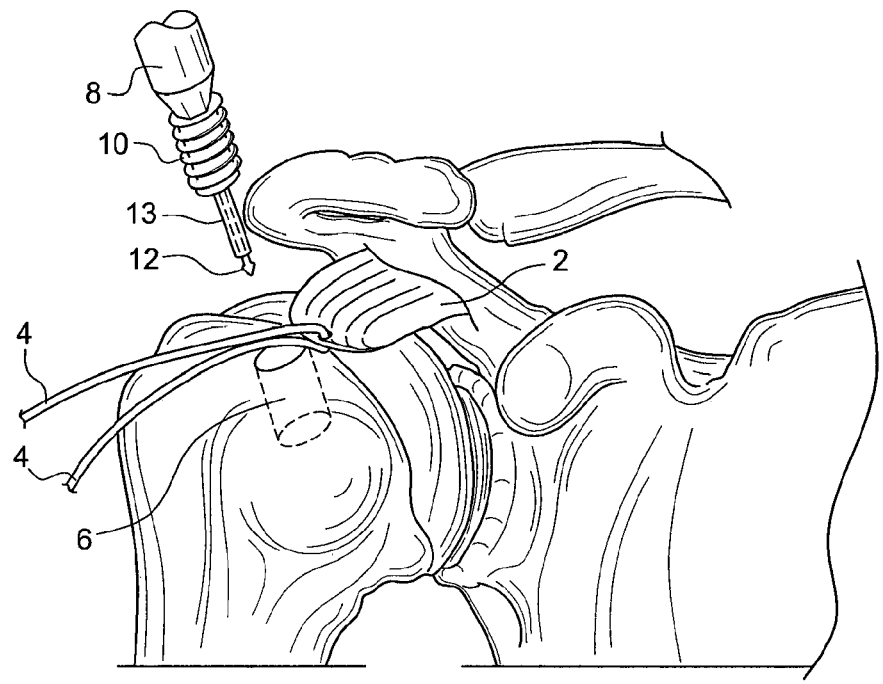
FIG. 2 is a perspective view depicting a next step in a method of rotator cuff repair according to the present invention.

Referring to FIG. 2, an anchor driver 8 is fitted with a cannulated threaded anchor 10 disposed over a guide wire 12. Anchor 10 also is received over an inner shaft 13 of driver 8. The inner shaft 13 is removable from within the driver 8 and can be advanced independently of driver 8. The tip of the guide wire 12 protrudes a few millimeters from the tip of the inner shaft 13 of driver 8. Two limbs of soft-tissue connector 4 are overlapped across the opening of the socket 6.

Figure 3:
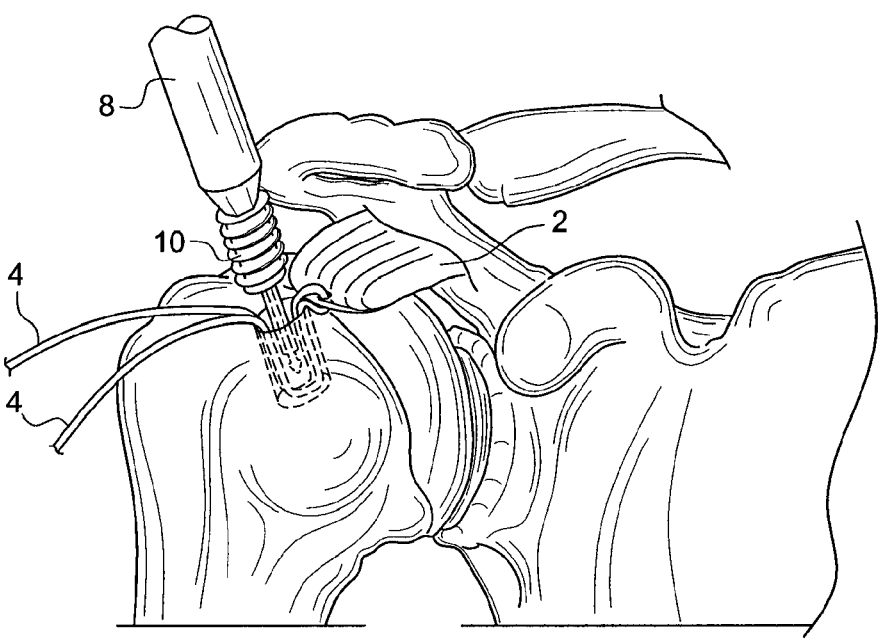
FIG. 3 is another perspective view depicting a further step in the method of rotator cuff repair subsequent to the step shown in FIG. 2.

Referring to FIG. 3, the exposed tip of guide wire 12 and the tip of inner shaft 13 are used to engage and urge the overlapped limbs of soft-tissue connector 4 into the bottom of the pre-formed socket 6. The length of soft-tissue connector urged into the socket is judged and adjusted so that the rotator cuff 2 is approximated to the preformed socket 6. With the soft-tissue connector held in place within the socket, the threaded anchor 10 is advanced over the guide wire and driven in until flush with the surface of the surrounding bone.

Figure 4:
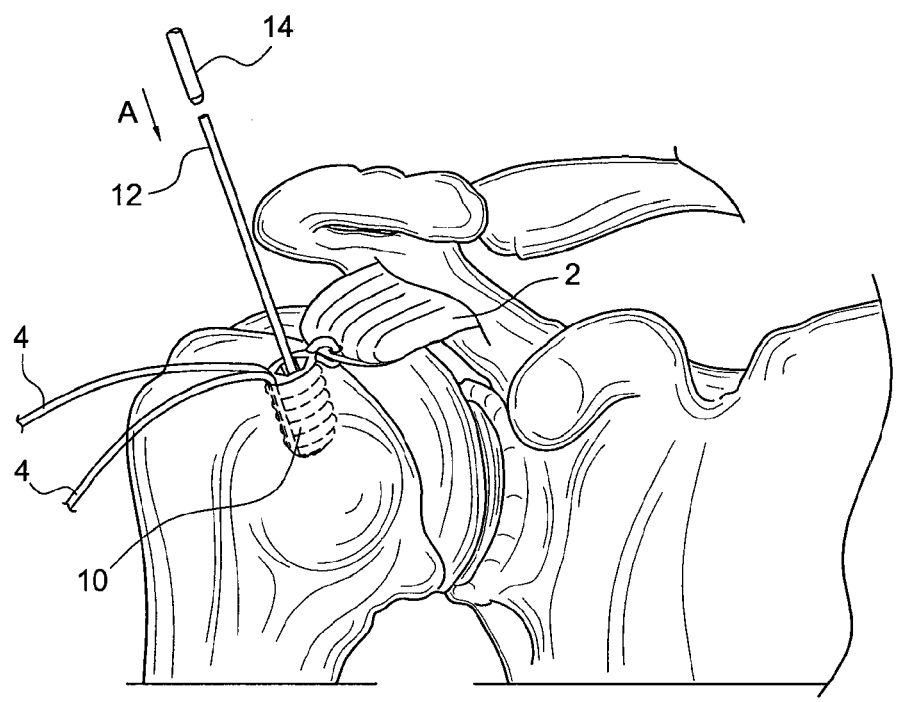
FIG. 4 is another perspective view depicting a further step in the method of rotator cuff repair subsequent to the steps shown in FIGS. 1-3, in which a cannulated pin is loaded onto a guide wire.

Referring to FIG. 4, once threaded anchor 10 is installed into socket 6, anchor driver 8 is removed, leaving guide wire 12 in place. A cannulated pin 14 is loaded onto guide wire 12. Cannulated pin 14 is advanced along the guide wire 12 and driven into the cannulation of threaded anchor 10. The cannulated pin 14 is urged flush with the surface of the surrounding bone. Preferably, the tip of cannulated pin 14 extends beyond the end of cannulated bone anchor 10 and penetrates into or through soft-tissue connector 4 to enhance securement within bone socket 6.

Figure 5:
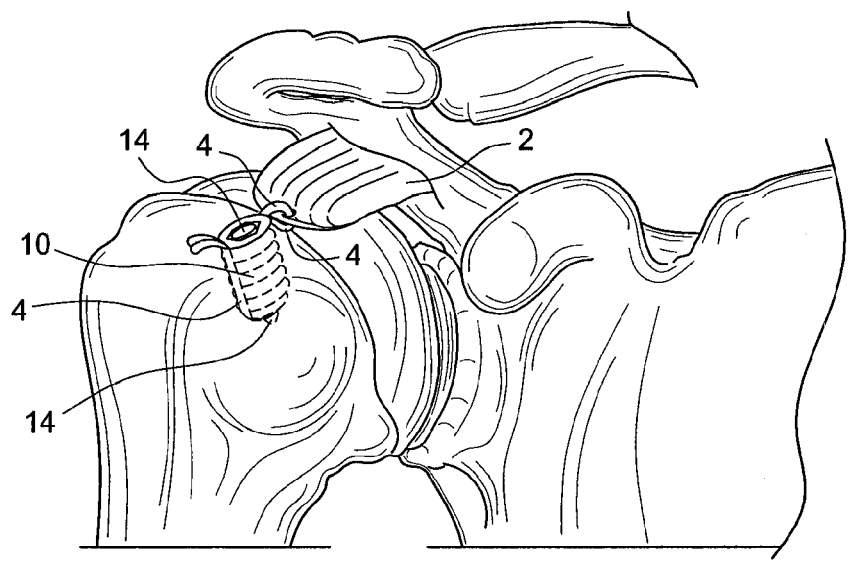
FIG. 5 is an enlarged perspective view depicting a concluding step in the method of rotator cuff repair subsequent to the steps shown in FIGS. 1-4, in which the cannulated pin has been installed and excess soft-tissue connector is cut off.

Referring to FIG. 5, the reattachment is finished by trimming off the exposed ends of soft-tissue connector 4 to be flush as possible with the surrounding bone. The steps above can be repeated to provide an additional anchor fixation point as indicated. Further, the present invention is not limited to using only one length of soft-tissue connector, but includes securement of additional soft-tissue connectors with one bone anchor, for example.

Figure 6:
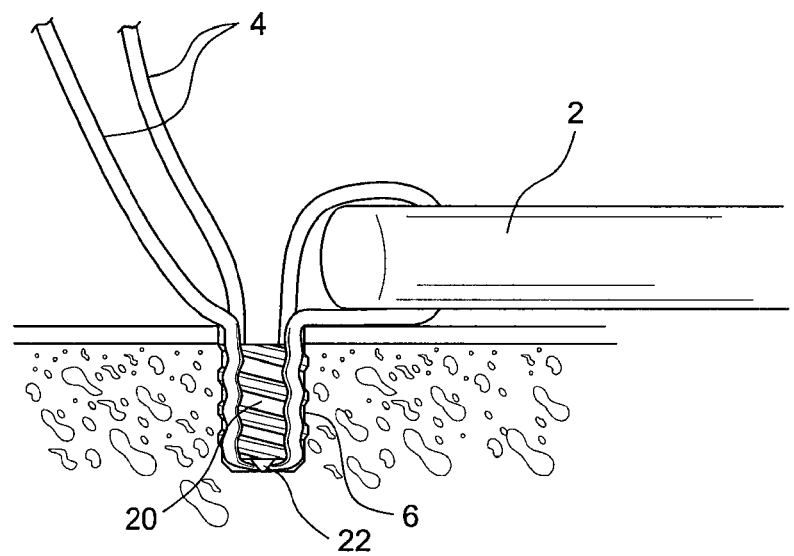
FIG. 6 illustrates use of an alternative anchoring device having a pointed tip or sharp spike for engaging soft-tissue connector by penetrating the tape and preventing slip.

FIG. 6 illustrates an alternative embodiment of the present invention in which a pointed-tip anchor 20 used in a method similar to that described above in connection with FIGS. 1-5. Pointed tip 22 of anchor 20 engages soft-tissue connector 4 at the bottom of socket 6. Anchor 20 can be cannulated or solid.

Figure 7:
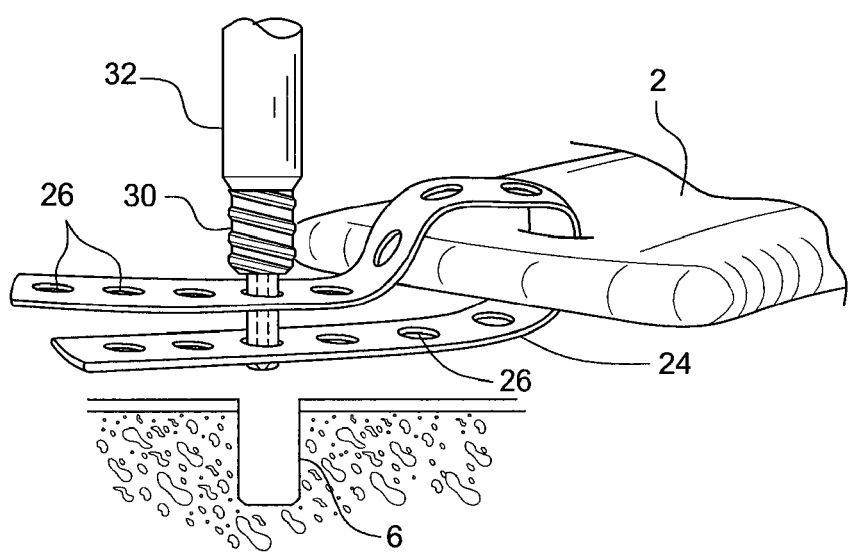
FIG. 7 illustrates use of an anchoring device and soft-tissue connector with reinforced perforations according to an alternative embodiment of the invention.

Referring to FIG. 7, a perforated soft-tissue connector 24 can be used in place of soft-tissue connector 4. Perforated soft-tissue connector 24 features perforations 26. In the double-limb construct shown in FIG. 7, an anchor 30 has a shaped tip that is inserted through two aligned perforations 26. A driver 32 is used to install the anchor 30 and the captured soft-tissue connector 24 into socket 6.

Figure 8:
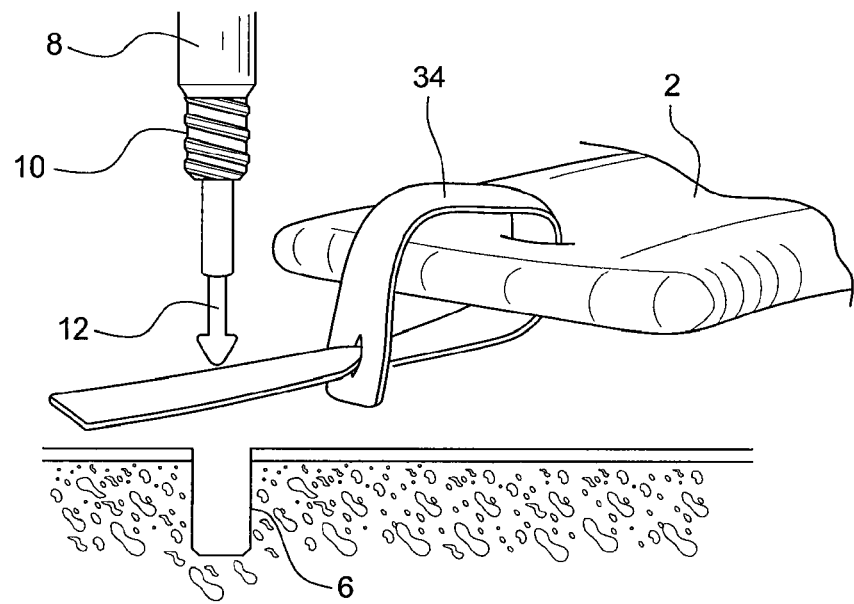
FIG. 8 illustrates use of a single-limb construct according to an alternative embodiment of the invention.
Figure 9:
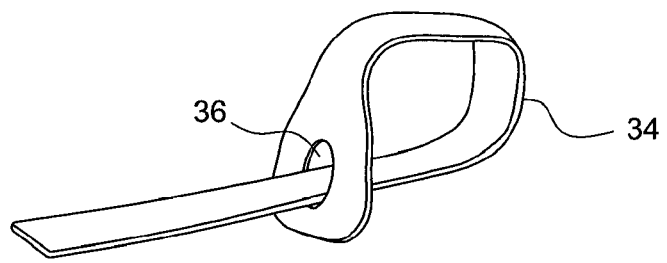
FIG. 9 illustrates an alternative development of a single-limb construct according to an alternative embodiment of the invention.

FIG. 8 illustrates a single-limb construct according another exemplification of the present invention. A length of a soft-tissue connector 34 is passed through rotator cuff 2 and then through itself using a suture needle, for example, to form a loop. The procedure is carried out in a similar fashion to that described above in connection with FIGS. 1-5. An alternative single-limb construct is shown in FIG. 9 in which soft-tissue connector 34 is provided with an eye 36. The single-limb of soft-tissue connector 34 can be simpler to engage and penetrate than a double-limb.

Figure 10:
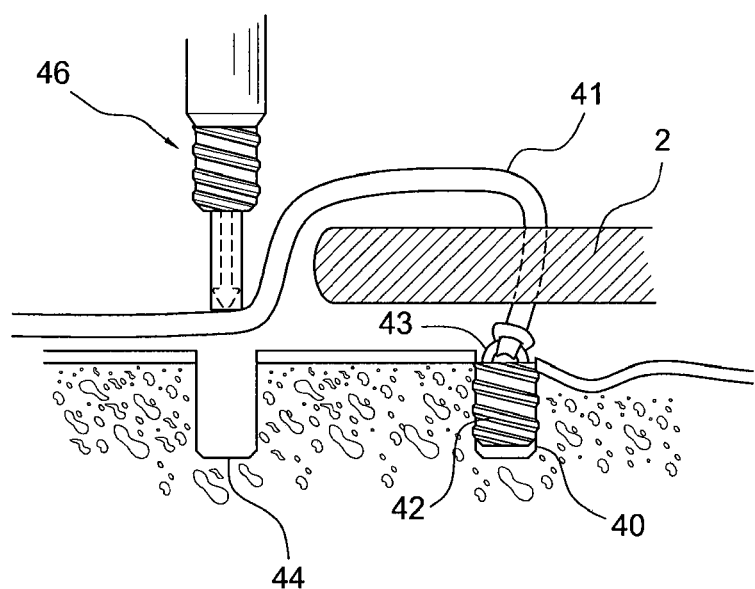
FIG. 10 illustrates use of a single-limb construct for double-row fixation according to another exemplification of the present invention.

FIG. 10 illustrates a single-limb construct used in double-row fixation according to another exemplification of the present invention. A medial socket 40 is prepared and a bone anchor 42 secures a length of soft-tissue connector 41 to the bone. The bone anchor 42 may have an eye 43 to which the soft-tissue connector 41 is secured. A lateral socket 44 is formed, and a length of the soft-tissue connector 41 is passed through the rotator cuff 2. The soft-tissue connector 41 is secured in socket 44 using an anchor/driver assembly 46 including an anchoring device similar to those described above. The anchor/driver assembly also can be configured similar to that shown and discussed, for example, in connection with FIGS. 7-11 of U.S. Pat. No. 6,544,281 to ElAttrache et al., discussed above and incorporated herein by reference.

Each of the anchor configurations noted above can be provided in a screw-in or press-in configuration. In a press-in configuration, the anchor can be installed by impact pressure, using a slap-hammer, for example. Alternatively, the anchor can be pressed in with gradual application of pressure. Various bone anchor configurations and installation techniques that are known to those of skill in the art, adapted to engage and secure soft-tissue connector as described herein, can be used without limitation in connection with the present invention.

Although the present invention has been described in connection with preferred embodiments, many modifications and variations will become apparent to those skilled in the art. The present invention is to be limited not by the specific disclosure herein, but only by the appended claims.

What is claimed as new and desired to be protected by Letters Patent of the United States is:

1. A surgical method comprising:
   forming a socket in bone;
   attaching a soft tissue connector formed as a flat narrow tape to soft tissue by looping the flat narrow tape through soft tissue and then through itself, to thereby form a flat, narrow connector limb attached to the soft tissue, wherein the step of looping the flat narrow tape through itself comprises passing the flat narrow tape through an eye of the flat narrow tape
   extending the connector limb over the opening of the socket;
   engaging and urging the connector limb into the socket with the tip of an instrument; and
   securing the connector limb within the socket by interference fixation by installing a bone anchor in the socket.

2. A surgical method as in claim 1, wherein the bone anchor is cannulated, the method further comprising holding the connector limb in the socket while installing the bone anchor into the socket.

3. A surgical method as in claim 2, wherein the cannulated bone anchor is threaded, and is driven into the bone socket by rotation.

* * * * *